(12) United States Patent
Baura

(10) Patent No.: US 6,186,955 B1
(45) Date of Patent: Feb. 13, 2001

(54) NONINVASIVE CONTINUOUS CARDIAC OUTPUT MONITOR

(76) Inventor: Gail D. Baura, 4547 Bermuda Ave., San Diego, CA (US) 92107

( * ) Notice: Under 35 U.S.C. 154(b), the term of this patent shall be extended for 0 days.

(21) Appl. No.: 09/192,944

(22) Filed: Nov. 16, 1998

(51) Int. Cl.⁷ .................................................. A61B 5/05
(52) U.S. Cl. ........................................................ 600/526
(58) Field of Search ................................ 600/526, 547; 128/924, 925

(56) References Cited

U.S. PATENT DOCUMENTS

| | | | |
|---|---|---|---|
| 4,898,176 | * | 2/1990 | Petre .................................... 600/526 |
| 5,505,209 | * | 4/1996 | Reining ................................ 600/526 |
| 5,509,424 | * | 4/1996 | Al-Ali .................................. 128/925 |
| 5,579,778 | * | 12/1996 | Baker .................................. 128/925 |

* cited by examiner

Primary Examiner—William E. Kamm
(74) Attorney, Agent, or Firm—James C. Weseman; The Law Offices of James C. Weseman

(57) ABSTRACT

Method and apparatus for continuous, non-invasive determination of cardiac output which processes a sequence of non-invasive cardiography signals which are quantitatively dependent upon cardiac output within a computer system and associated neural network capable of generating a single output signal for the combined input signals, wherein the neural network applies weighting factors determined during a training phase to force the output signal to match the known value of cardiac output determined by invasive means and reports the single output signal as the determined value of cardiac output.

7 Claims, 3 Drawing Sheets

NONINVASIVE CONTINUOUS CARDIAC OUTPUT MONITOR

TECHNICAL FIELD

The present invention relates to continuous hemodynamic monitoring and, more specifically, to monitoring cardiac output by non-invasive cardiography.

BACKGROUND OF THE INVENTION

Hemodynamic monitoring of the heart can provide valuable physiological information regarding the functional state of the myocardium, which is intimately related to its mechanical behavior. The quantitative measurement of blood flow, or cardiac output (CO), defined as the total blood volume pumped by the heart per unit time, is one of the most useful parameters in assessing cardiac capability. It reflects not only the functional state of the heart but also the response of the entire circulatory system to acute and chronic disease and the impact of therapeutic interventions. Basal CO is related to body size and varies from 4 to 7 liters per minute in adult humans.

However, CO is also one of the more difficult parameters to measure. The calculation of CO includes a determination of both the heart rate (HR) and the heart stroke volume (SV), from which CO can be estimated.

The HR can be determined in a number of ways, among which the phonocardiogram is considered to be the most accurate method. However, due to practical difficulties the phonocardiogram method is generally not employed for any continuous or long-term monitoring. In practice, HR is most typically determined by the electrocardiogram (ECG). The analog ECG signal typically displays electrocardial events as perturbations, usually referred to as waves. The heartbeat is most clearly reflected in the ECG signal as an R wave peak between a pair of adjoining Q and S wave valleys. The commonly used method of automatically identifying the QRS wave pulses is the threshold method, in which the rate of voltage change between consecutive data points of the ECG signal is monitored and compared with a threshold value, where slopes exceeding the threshold value are deemed to be associated with a portion of the QRS pulse. While this method commonly detects the interval between consecutive R waves successfully more than eighty percent of the time, it typically has difficulty in dealing with sources of irregular signal components such as pacemakers, muscle noise, and 60 Hz interference, as well as nearby T or P waves which may also be associated with significant slope changes. More significantly, CO monitoring cannot be accomplished with an ECG alone, as this measurement does not reflect the true pumping action of the heart.

Both invasive and non-invasive methods are available for measurement of the SV component of CO, or CO directly. Traditionally, CO has been measured invasively by using one of various indicator-dilution methods. The current accepted standard is thermodilution, where a chilled dextrose or saline solution is used as the indicator. A catheter incorporating a thermistor is inserted through the right atrium and right ventricle, and into the pulmonary artery. The solution is injected into the right atrium as a 5–10 mL bolus, where it mixes with venous blood, causing the blood to cool slightly. Changes in blood temperature occur over time as the solution bolus is washed out of the heart, then passes by the thermistor located at the tip of the catheter in the pulmonary artery, and result in a detectable temperature change in the blood flowing through the artery proportional to the relative volumes of solution bolus and blood. Blood temperature is measured to create a thermal dilution curve from which CO is derived.

Although it is the standard in clinical medicine, thermodilution has several disadvantages. Because of heat loss through the catheter wall, several 5 mL injections are required to obtain a consistent value for CO. If the CO is low, leading to a broad dilution curve, it is difficult to obtain an accurate value. Respiration-induced variations in the pulmonary arterial blood temperature also confound the dilution curve when it is of low amplitude. Risks from the procedure include line sepsis, bacterial endocarditis, large vein thrombosis, cardiac arrhythmia, pneumothroax, and increased mortality (Connors, et al., JAMA, 276:889–897, 1996). Thus, although the invasive methods are considered the most accurate, the risks associated with their use are often an unacceptable trade-off, for they require direct access to the arterial circulation. In addition, older invasive methods are not suitable for repetitive measurements and normally cannot be performed outside a hospital. Furthermore, invasive methods are very demanding in terms of time consumption and the need for skilled personnel.

As an option to invasive, intermittent methods, recent research has focused on obtaining CO from noninvasive, continuous methods. Emerging noninvasive techniques include the partial carbon dioxide rebreathing Fick technique, the echo-doppler technique and endotracheal impedance cardiography. A more developed technique is impedance cardiography, also known as thoracic electrical bioimpedance or impedance plethysmography. Impedance cardiography has been found to be a non-invasive method with the potential for monitoring the mechanical activity of the heart with virtually no risk. It can be conveniently handled by nursing and non-technical staff. It can usually tolerate moderate patient movement and can be left unattended for continuous and long-term monitoring. With this method, the SV is estimated; CO is then obtained as the product of SV times HR. For impedance cardiography, a constant current source (I), of approximately 50 to 100 kHz, is injected across the thorax. The resulting voltage (V) is used to estimate the impedance, assuming the impedance is purely resistive, as $Z=V/I$. Because the skin impedance is two to ten times the value of the underlying body tissue impedance, four, rather than two, electrodes are used in a configuration which eliminates the skin impedance from the impedance measurement.

U.S. Pat. No. 3,340,867, now RE 30,101, to Kubicek et al. discloses an impedance plethysmography system which employs four electrodes, two around the neck and two around the torso of a patient, to provide an impedance difference signal from the two center electrodes. The outermost pair of electrodes apply a small magnitude, high frequency alternating current to the patient while the inner pair of electrodes are used to sense voltage levels on the patient above and below the patient's heart. The impedances of the patient at each of the inner pair of electrodes could be determined from the sensed voltages and known applied currents.

According to Kubicek et al., SV is related to impedance (Z) as follows:

$$SV = R \cdot (L/Z_0)^2 \cdot (VET) \cdot (dZ/dt_{max})$$

where R is blood resistivity, L is the distance between the inner voltage sensing electrodes, $Z_0$ is the mean thoracic impedance determined from the inner, voltage sensing electrodes, VET is the ventricular ejection time and $dZ/dt_{max}$ is the maximum negative slope change of the time-differentiated impedance signal, which is the time-differentiated difference between the impedances determined at the center two electrodes. The above equation is referred to as Kubicek's equation.

Kubicek's equation is based upon a parallel column model of the thorax in which it is assumed:

(1) the thorax is a cylinder, consisting of two electrically conducting tissue paths, also of cylindrical form with uniform cross-sectional areas and homogenous conducting materials, the first path being the blood with a relatively low resistivity and the second path being all other tissues with relatively high resistivities;

(2) the relationship between the maximum impedance change and the stroke volume during the cardiac cycle is linear;

(3) impedance measurements of the individual specific tissue volumes are not very useful in developing the model (the parallel columns model relies on the intact thoracic measurements); and (4) at 100 kHz frequency, a physiologically safe frequency, the relative thoracic impedance changes are at a maximum, the effects of polarization are negligible, and the reactive component of impedance is small, especially when compared to the real component, so that the reactance could be ignored in determining impedance with only a small error.

Unfortunately, this technology was never widely accepted because of its poor correlation with invasive methods. A major source of inaccuracy was the requirement that the maximum negative slope change of the time-differentiated impedance be calculated. Derivatives are inherently noisy, and the early methods employed in calculating this slope change were unreliable.

More recently, Sramek improved the original Kubicek relationship between impedance and stroke volume (U.S. Pat. No. 4,450,527). Assuming that the thorax can be modeled as a frustocone, stroke volume is determined as:

$$SV=(L^3/4.25Z_0) \cdot VET \cdot (dZ/dt_{max})$$

This improved relationship was based on a better assumption of the shape of thorax, and Sramek's disclosure provided a method to minimize ventilation noise artifact. While probably only modestly effective, the averaging of the impedance enabled measurements to be acquired during normal breathing. (Until this innovation, measurements could only be made while the patient held his breath). Even with these improvements, the correlation with thermodilution remained weak.

In a recent study, the accuracy of Sramek's BoMed NCCOM3 impedance cardiograph was evaluated against Thermodilution in 19 cardiac patients ranging from 29 to 75 years. Initially after cardiac surgery, the correlation coefficient square, $r^2$, was $r^2=0.30$ (p=0.002) between the two methods. This measure decreased to $r^2=0.26$ (p=0.004) 2 to 4 hours after surgery (Yakimets, et al., Heart Lung, 24:194–206, 1995). Therefore, approximately 30% of the variance from thermodilution can be accounted for using the Sramek equation. Thus, the Sramek model illustrates some improvement and accuracy over the Kubicek model but its major assumptions are still similar to those of the Kubicek model.

Despite its advantages, impedance cardiography has not been well accepted by clinicians for two primary reasons:

(1) poor correlation of the methods and models with the results of the more accepted invasive techniques; and (2) a relatively high dependance on skilled technical operators.

It is believed that poor correlation, the primary reason, can be traced back to a single source, namely the continuing inability to relate impedance cardiography and its mathematical model directly to cardiac physiology.

Ziang Wang's Ph.D. dissertation at Drexel University further improved system accuracy in impedance cardiography. Using time-frequency analysis, which is extremely resistant to noise artifact, the maximum negative slope change of the impedance derivative was calculated. Calculation of the HR was also improved using time-frequency analysis. This development was disclosed in two patents (U.S. Pat. Nos. 5,309,917 and 5,443,073) and is incorporated into the IQ System supplied by Renaissance Technologies.

In a study of 68 cardiac patients whose mean age was 45±20 years, 842 simultaneous thermodilution and IQ System measurements were made in emergency rooms (n=36), operating/postanesthesia rooms (n=4), and surgical/medical intensive/coronary care units (n=38). The resulting correlation coefficient squared was $r^2=0.74$ (p<0.01) between the two methods (Shoemaker, et al., Crit Care Med. 22:1907–1912, 1994). Therefore, approximately 75% of the variance from thermodilution can be accounted for using the Wang method.

According to Shoemaker, et al., the difference between thermodilution and impedance CO measurements diverged when the control baseline impedance was less than 20 ohms. Reduced baseline impedance occurs with increased fluid in the chest, associated with pulmonary edema and plural effusion. With increased intrathoracic fluids, the injected current bypassed normal thoracic structures, leading to inaccurate estimates of CO, compared to thermodilution measurements. Furthermore, in patients where high CO values were associated with tachycardia and cardiac dysrhythmias, impedance cardiography underestimated corresponding thermodilution values. Since the dZ/dt waveform reflects changes in impedance throughout the cardiac cycle, the pulsatile component of flow dominates in impedance CO calculations. However, the proportion of pulsatile systolic flow to the more constant diastolic flow is less in tachycardia and hyperdynamic states.

One system which has used a neural network to compensate for various shortcomings in measuring CO is described in U.S. Pat. No. 5,579,778. However, this system relies on invasive measurements of CO, and thus does not address the shortcomings of invasive monitoring generally.

It would be desirable to provide non-invasive monitoring to estimate stroke volumes, cardiac output and related cardiac function parameters which correlate more closely with the stroke volumes, cardiac outputs and the like determined by means of recognized, accepted invasive procedures, but which does not require of operators the technical skills required by current systems, thereby permitting relatively long-term monitoring of the patient's condition.

It would also be desirable to compensate for the apparent nonlinearity between invasive and non-invasive measurements of cardiac output.

DISCLOSURE OF THE INVENTION

It is an object of the present invention to provide a method and apparatus for collecting and processing non-invasive impedance cardiography data for a more accurate estimation of cardiac output.

It is a further object of the present invention to provide a method and apparatus for estimating cardiac output utilizing a neural network as a system for processing input data and ultimately calculating the cardiac output.

It is yet another object of the present invention to provide a method and apparatus for generating a body of training data for use as part of a neural network to assist in estimation and determination of cardiac output derived from the generated data having a nonlinear relationship with the values monitored.

A still further object of the present invention is to provide a method and apparatus for determining cardiac output despite the occurrence of noise and other signal corrupting influences.

Another object of the present invention is to provide a method and apparatus for unattended non-invasive impedance cardiography estimation of cardiac output.

Yet another object of the invention is to provide a method and apparatus for non-invasive impedance cardiography estimation of cardiac output when the total cardiac flow volume is low and the technique would normally be inapplicable.

These and other objects are realized in a method for non-invasive measurement of impedance cardiography data. The method comprises the steps of (a) generating a sequence of non-invasive cardiography signals which are quantitatively dependent upon cardiac output, (b) transmitting and processing the signals within a computer system and associated neural network capable of generating a single output signal for the combined input signals, wherein the neural network applies weighting factors determined during a training phase to force the output signal of the neural network to match the known value of cardiac output determined by invasive means; and (c) reporting the single output signal as the determined value of cardiac output.

Also provided is an apparatus for correlating an estimation of cardiac output derived from non-invasive means to a determination of cardiac output derived from invasive means.

The invention can be integrated into an appropriate non-invasive monitor, such as an impedance cardiography monitor, or employed as a supplement to an existing monitor. The method utilizes a neural network to model the nonlinearity between the two cardiac output measurements, i.e. the invasive and non-invasive measurements. During the training phase of the invention, simultaneous invasive, e.g. thermodilution, and non-invasive, e.g. impedance cardiography, cardiac output patient values are input to a neural network to tune its weight parameters. During the post-training phase, the tuned weights are then programmed in software. Thereafter, when a cardiac output estimate is made by the non-invasive cardiography monitor, it is input to the apparatus, which uses the weights to adjust the estimate and report a compensated cardiac output estimate. One form of invasive cardiac output value measurement can be provided by thermodilution.

DETAILED DESCRIPTION OF THE INVENTION

The present invention provides a method and apparatus to compensate for the apparent nonlinearity between invasive, e.g. thermodilution, and non-invasive, e.g. impedance cardiography, measurements of cardiac output. The method comprises the steps of (a) generating a sequence of non-invasive cardiography signals which are quantitatively dependent upon cardiac output, (b) transmitting and processing the signals within a computer system and associated neural network capable of generating a single output signal for the combined input signals, wherein the neural network applies weighting factors determined during a training phase to force the output signal of the neural network to match the known value of cardiac output determined by invasive means; and (c) reporting the single output signal as the determined value of cardiac output. The invention can be integrated into an appropriate non-invasive cardiography monitor or employed as a supplement to an existing cardiography monitor.

Figure 2:
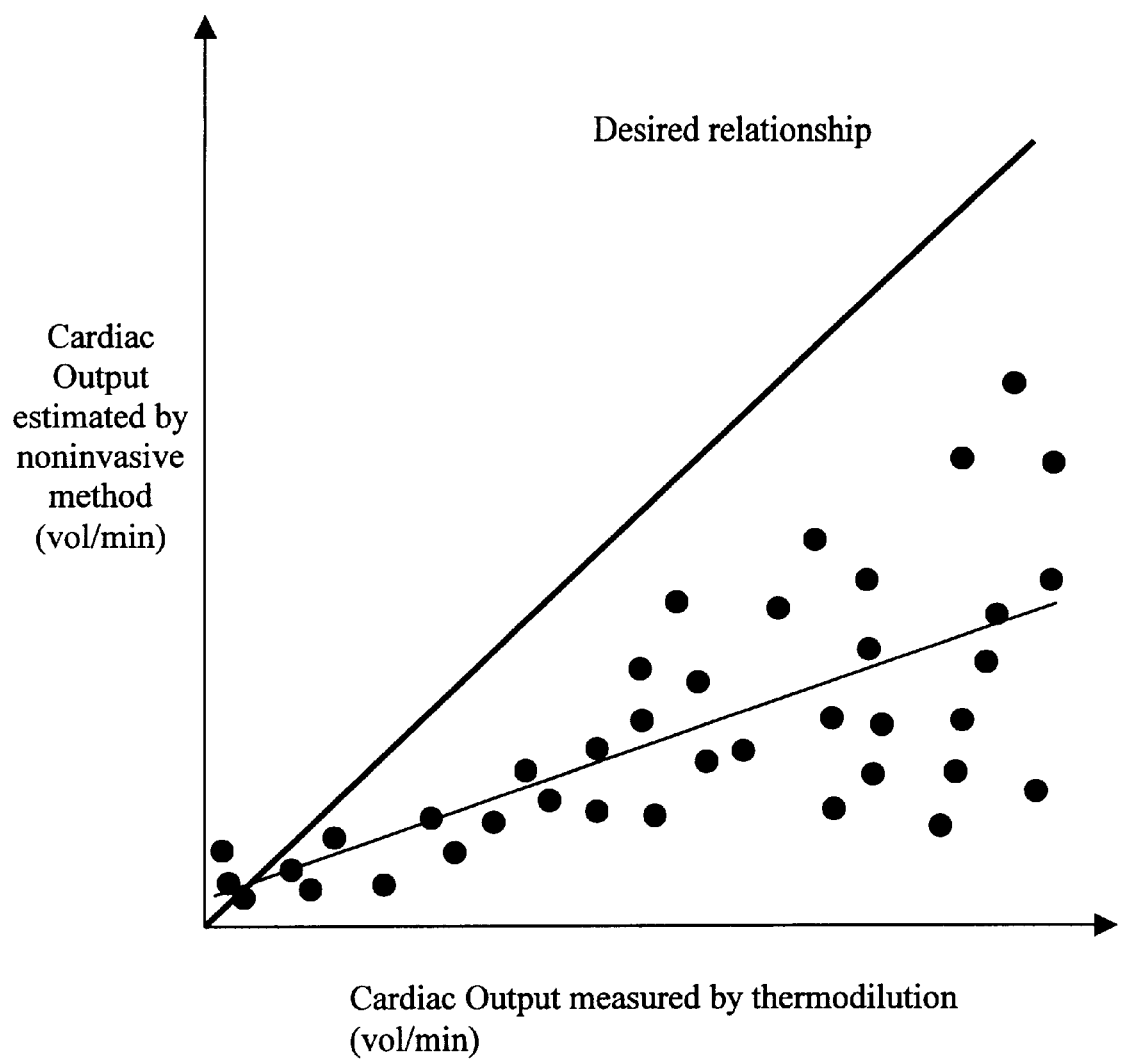
FIG. 2 graphically depicts a plot of the relationship of cardiac output determinations obtained by invasive and noninvasive techniques, including the idealized equivalent relationship.

The present method utilizes a neural network to model the nonlinearity between the diverse cardiac output measurements, as depicted in FIG. 2. During the training phase of the invention, simultaneous cardiac output patient values, e.g. thermodilution and impedance cardiography values, are input to a neural network to tune its weight parameters. During the post-training phase, the tuned weights are then programmed in software. Thereafter, when a cardiac output estimate is made by the non-invasive cardiography monitor, it is input to the apparatus, which uses the weights to adjust the estimate and report a compensated cardiac output estimate which more closely adheres to the idealized relationship depicted in FIG. 2.

Certain abbreviations will be used interchangeably with the following terms:

Heart Rate (HR): the number of times the heart contracts each minute.

Stroke Volume (SV): the volume of blood pumped out by a ventricle (in particular the left ventricle) with each contraction of the heart.

Cardiac Output (CO): the amount of blood pumped out of the heart into the systemic circulation each minute.

Compensated Cardiac Output (CCO): a determined non-invasive estimate of CO which has been correlated to a CO estimate derived by alternate invasive means.

Invasive Cardiac Output Measurement

In order to more clearly describe the operation of the present invention, the invasive monitoring of CO will be generally described for example by reference to thermodilution techniques well known in the art. In accordance with such techniques, CO has been measured invasively by thermodilution, where a chilled dextrose or saline solution is used as the indicator. A catheter incorporating a thermistor is inserted through the right atrium and right ventricle, and into the pulmonary artery. The solution is injected into the right atrium as a 5–10 mL bolus, where it mixes with venous blood, causing the blood to cool slightly. Changes in blood temperature occur over time as the solution bolus is washed out of the heart, then passes by the thermistor located at the tip of the catheter in the pulmonary artery, and result in a detectable temperature change in the blood flowing through the artery proportional to the relative volumes of solution bolus and blood. Blood temperature is measured to create a thermal dilution curve from which CO is derived. This measurement data is then utilized in the practice of the present invention in the manner hereinafter described.

One reported improvement to the general technique described above is provided in U.S. Pat. No. 5,579,778, the entire contents of which is incorporated herein by this reference. This system modified the catheter in two ways.

First, the lumen injection port in the right atrium was closed, because the solution bolus is not injected into the blood of the heart. Second, a heat exchanger was put in place of the injection port on the catheter. The heat exchanger was a thin but strong membrane that allowed for heat exchange with blood in the vena cava. The chilled saline bolus was circulated between the membrane and the catheter. The blood returning to the heart was thus cooled as it passes by the membrane, continued through to the right ventricle, flowed into the pulmonary artery, and passed by the thermistor at the distal end of the catheter that measures the temperature depression of the venous blood mixture.

However, it should be clearly understood that the present invention will be able to use numerous alternative invasive systems, including alternative indicator-dilution systems, which differ from the described system in numerous particulars.

Non-Invasive Cardiac Output Measurement

In order to more clearly describe the further operation of the present invention, the non-invasive monitoring of CO will be described, for example by reference to impedance cardiography monitoring, generally in accordance with the disclosures of U.S. Pat. Nos. 3,340,867, RE 30,101, 4,450, 527, 5,309,917 and 5,443,073, the entire contents of which are each incorporated herein by this reference. However, it should be clearly understood that the present invention will find use in numerous alternative non-invasive systems, including alternative impedance cardiography CO systems, which differ from the described systems in numerous particulars.

In operation, a cardiographic impedance monitoring system will be coupled to a patient for use. The system will typically include a first, outer pair of electrodes, and two pairs of parallel connected, desirably spot-type, skin electrodes. The first pair of electrodes are applied to the patient's skin on opposite upper and lower sides of the heart, typically equally spaced from the heart.

The pairs of parallel coupled electrodes are applied to the patient on opposite upper and lower sides of the heart respectively and between the first or outer pair of electrodes. Each pair of electrodes are typically positioned on opposite lateral sides of the patient at uniform heights above and below the heart. Again, the electrode pairs are typically equally spaced from or otherwise symmetrically positioned with respect to the heart. A pair of conventional electrocardiogram electrodes are also employed.

Desirably, all electrodes are coupled through a signal pickup and preprocessor and then through an analog to digital converter to a data processor. A color video monitor and an optional hard copy printer are desirably provided under the control of the processor. While a separate pair of electrocardiogram electrodes will desirably be employed, it will be appreciated that certain of the electrode pairs might also be configured to generate an electrocardiogram signal by suitable processing of their signals. The outer pair of electrodes are used to apply a fluctuating, typically alternating current through the patient between those electrodes while the remaining electrode pairs are provided to sense voltage levels on the patient from which thoracic impedance is determined.

The general advantages possessed by tetrapolar electrode configurations over bipolar electrode configurations are that the voltage sensing electrodes are substantially free of skin impedance, can measure impedance with less electrode-interface artifact and offer the possibility of providing a more uniform current density distribution in the segment of interest in the patient.

There will generally be a distortion in the current density distribution in patients in the vicinity of the current electrodes, known as the edge effect. In addition to edge effects, uniform current distribution is disturbed by the superposition of a relatively highly conductive sphere, namely the heart, and the relatively low conductivity of air in the lungs in the region between the electrodes. The current distribution has been reported to be more uniform in the central region between the electrodes as a function of the width of spacing between the electrodes. In addition, it has been reported that the positions of the current electrodes relative to those of the voltage detecting electrodes are also important to ensure uniform current distribution. It is thought that if the distances between adjoining pairs of the electrodes are sufficiently great, the edge effect is essentially minimized and the impedance measurement becomes stable.

The signal pick-up and preprocessor can be a Minnesota Impedance Cardiograph (MIC) Model 304B (Sorocom, Inc., MN), or equivalent system. The MIC 304B provides a high frequency (approximately 100 kHz), low amplitude (4 mA RMS) alternating current at pick-ups provided for the electrodes. Pick-ups are also provided for the parallel coupled voltage sensing electrode pairs and for the ECG electrodes.

The preprocessor generates and outputs four analog signals: the mean thoracic impedance signal ($Z_0$), the change in thoracic impedance signal ($\delta Z$), the time-derivative impedance signal (dZ/dt) and the electrocardiogram signal (ECG). The mean thoracic impedance signal, $Z_0$, is the impedance difference sensed between the sensing electrode pair. The change in thoracic impedance signal, $\delta Z$, is an amplification of the original $Z_0$ signal from which the DC component has been removed. The time-derivative impedance signal, dZ/dt, is the time derivative of the amplified $\delta Z$ signal. The ECG signal is conventional. The dZ/dt signal is conventionally inverted so that its maximum slopes will appear positive, thereby enabling the clinician to observe the cardiac event in a more familiar manner. Cardiac events appear in the impedance and ECG signals as perturbations or "waves". ECG waves related to each heartbeat are also noted on the ECG signal at P, Q, R, S and T. In many cases, however, the identification of individual waves in either signal is not so apparent.

The analog signals from the preprocessor are passed to an analog to digital (A/D) converter. Typically, the A/D converter is configured for differential conversion at a sampling rate of 500 Hz for each of the analog signals with a twelve bit resolution in offset binary format. The A/D converter may be, for example, a Data Translation Model DT 2811/ PGH.

The digitized signals are typically passed into an allocated memory such as a hard disk or RAMDISK in or associated with the processor and stored in binary format for subsequent processing. The operational steps of the processor in determining heart rate, CO and a variety of other parameters reflecting cardiac performance are generally as described in U.S. Pat. Nos. 5,309,917 and 5,443,073, although other formats will readily suffice.

Typically, the system will be configured to be operable in a predata signal processing mode in which the preprocessor and A/D converter operate to pass binary data signals to the processor which formats the signals for real-time or essentially real-time display on the monitor. After the clinician has verified successful signal gathering and digitization through the display, the data signal processing for cardiac parameter determinations are begun. Typically the processor will initialize the necessary calculation variables and begin storing the binary ECG and impedance signal data in a hard disk or RAMDISK in the binary format for subsequent processing.

Initial data processing includes converting the stored binary impedance and ECG signal data into decimal integer format and reading the decimal format data into a working memory area of the processor in predetermined time period blocks for processing. The ECG signal data is first processed by low-pass (LP) and high-pass (HP) filtering, then differentiated and thereafter non-linearly scaled or transformed. The filtered, differentiated, scaled ECG data is then further adaptively processed to detect the R wave peaks, which are used to identify the cardiac cycles of the heartbeat, and to validate the detected peaks. If valid, the processor stores the time of occurrence of each validated peak as the peak of an R wave in the ECG signal block. In the preferred embodiment, the resultant impedance cardiography-predicted CO, HR, mean thoracic impedance, maximum derivative of the impedance, thoracic length, and ventricular ejection time data are then utilized in the practice of the present invention in the manner hereinafter described.

In alternative embodiments, CO parameters may be obtained from monitors based on other noninvasive methods. With the partial carbon dioxide ($CO_2$) rebreathing Fick technique, an estimate of CO is obtained by measuring the change in carbon dioxide during ventilation. The ratio of the change in $CO_2$ production ($VCO_2$) and endtidal $CO_2$ ($etCO_2$), in response to a brief period of rebreathing, is used to calculate pulmonary capillary blood flow (PCBF). Periodic blood gas measurements are then used to estimate intrapulmonary shunt blood flow (Qs). Cardiac output is calculated as the sum of PCBF and Qs. In such alternate embodiments, the resultant $CO_2$ Fick parameters $VCO_2$, $etCO_2$, PCBF, Qs, and CO can also be passed to a neural network for further processing.

In alternative embodiments which employ the echo-doppler technique, two ultrasound sensors are used for measurements. The doppler sensor enables calculation of the aortic blood velocity (ABV), which is proportional to the doppler shift frequency. The echograph enables calculation of the aortic cross section (ACS). The product of ABV and ACS is the CO. This calculation can be made with a large ultrasound system or with a more portable monitor which utilizes a single transophageal probe, on which the ultrasound sensors are mounted. In an alternate embodiment, the resultant echo-doppler parameters ABV, doppler shift frequency, ACS, and CO can also be passed to a neural network for further processing.

A new technique recently tested in swine measures CO in the ascending aorta with an endotracheal tube with multiple electrodes. The electrodes measure the changes in electrical impedance. Again, in alternative embodiments of the invention employing such a technique, the resultant CO, HR, mean impedance, maximum derivative of the impedance, distance between electrodes, and ventricular ejection time data may be passed to a neural network for further processing.

Processing of Cardiac Output Signals with a Neural Network

Figure 1:
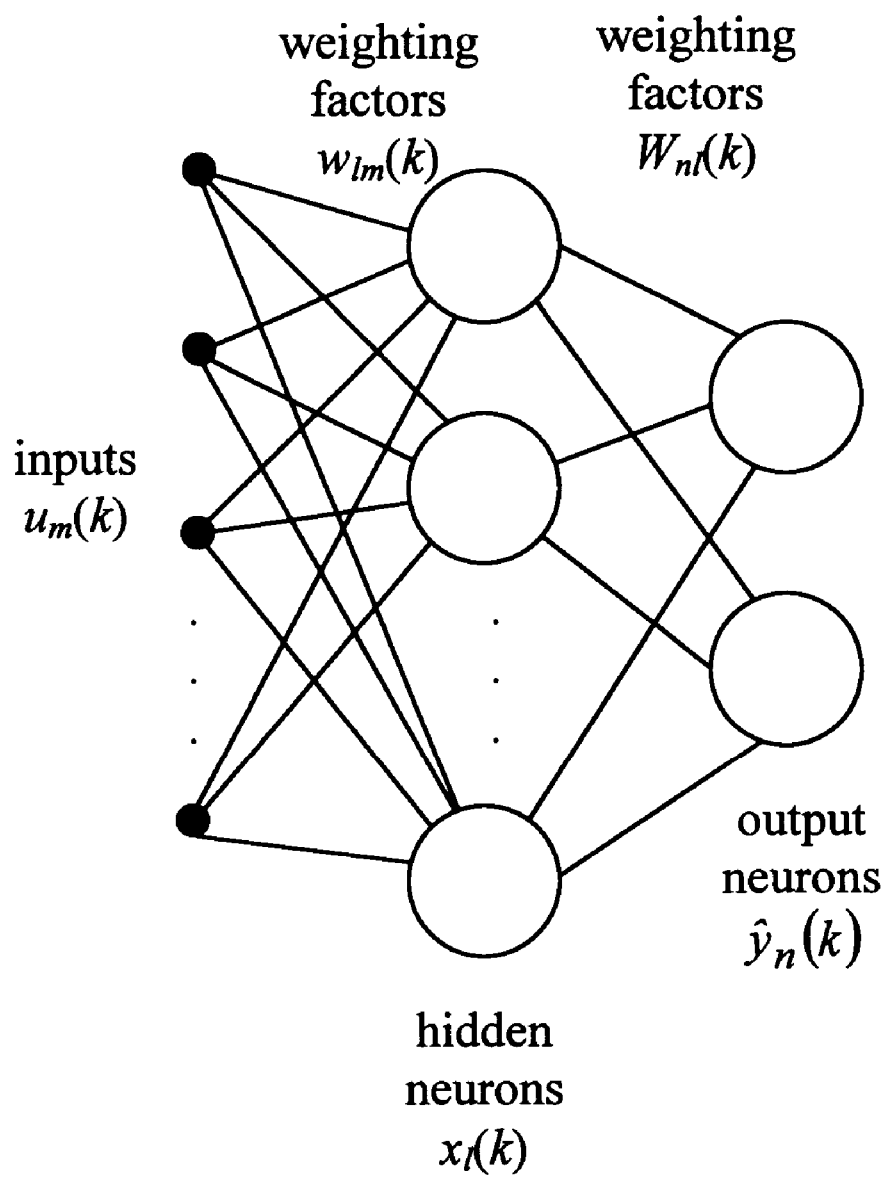
FIG. 1 graphically depicts an embodiment of a generalized neural network comprising a feedforward neural network in accordance with the present invention.

FIG. 1 is a graphic representation of a generalized neural network structure. A neural network is a mathematical model, similar to neural cells of a brain which are linked together to create a network that can be taught or trained to identify sets of inputs which appear to be similar to example input sets previously supplied to the network in a training situation. Once a neural network is trained, it provides a means of computing an appropriate output signal (such as CO) when presented with a given input signal (such as an impedance cardiography waveform). Training data, for example derived from invasive measurement, is used to modify the neural network weights as applied to various nodes making up the network until the network is optimized in a stochastic sense to provide the appropriate output for a given input.

Utilizing a neural network results in increased accuracy of the correlation with invasive monitoring, due to the ability of the neural network to view the waveform as a whole, rather than concentrating on limited features of the curve, such as curve area. As shown in FIG. 1, the basic building block of a neural network is the neuron (the sum of inputs to a single node in the hidden layer and its output to the output layer). Each cell or neuron has an input side that receives input data, shown here as $E_k$, and an output side $O_i$ as illustrated. The input side receives multiple signals that are weighted using weighting factors $W_{jk}$ and $W_{ij}$ determined during training, while the output side $O_i$ is usually comprised of a single output signal.

While many neural network architectures can be utilized in order to process the raw signals from the non-invasive cardiography monitor and provide a compensated CO (CCO) signal, one preferred embodiment is the feedforward neural network, which uses back propagation of error to tune its weights. A neural network may be specified in terms of its architecture. This includes the (i) number of nodes and the interconnection relationships between them, (ii) node characteristics such as input/output functions, and (iii) learning or training rules which define the method by which the node interconnections are adapted during training. The power of a neural network arises in part from the use of nonlinear functions to process node inputs and the use of parallel distributed processing wherein a given piece of information is not restricted to a single node but may appear as input to many nodes which may operate on the network inputs concurrently. The preferred network contains two layers: A hidden layer with several nodes, $V_j$, and an output layer, $O_i$, provides the CCO estimate. For each pair of simultaneous impedance cardiography and thermodilution CO data, the network is tuned, such that error between the network output and the thermodilution value is minimized.

The number of weights, $W_{jk}$ and $W_{ij}$, in the network depends on the number of inputs, hidden nodes, and output nodes. In the preferred embodiment, impedance cardiography-predicted CO, heart rate, mean thoracic impedance, maximum derivative of the impedance, thoracic length, and ventricular ejection time are passed to 3 hidden nodes, after each being scaled by a multiple of 10 to a value between −1 and +1. A feedforward network with 6 inputs, 3 hidden nodes, 1 output, and 21 weights can be visualized from the network shown in FIG. 1. The diagram should only be considered illustrative of the neural network concept. In practice, there can be many hidden layers comprised of a varying number of nodes, as well as multiple output nodes in the output layer. Within the network, each node takes inputs, multiples them by corresponding weights, sums them, and outputs the hyperbolic tangent or another chosen activation function, g(h), of this sum. The output node is calculated as:

$$O_i = g\left\{\sum_j W_{ij} g\left\{\sum_k W_{jk} E_k\right\}\right\}$$

Equation 1

Figure 3:
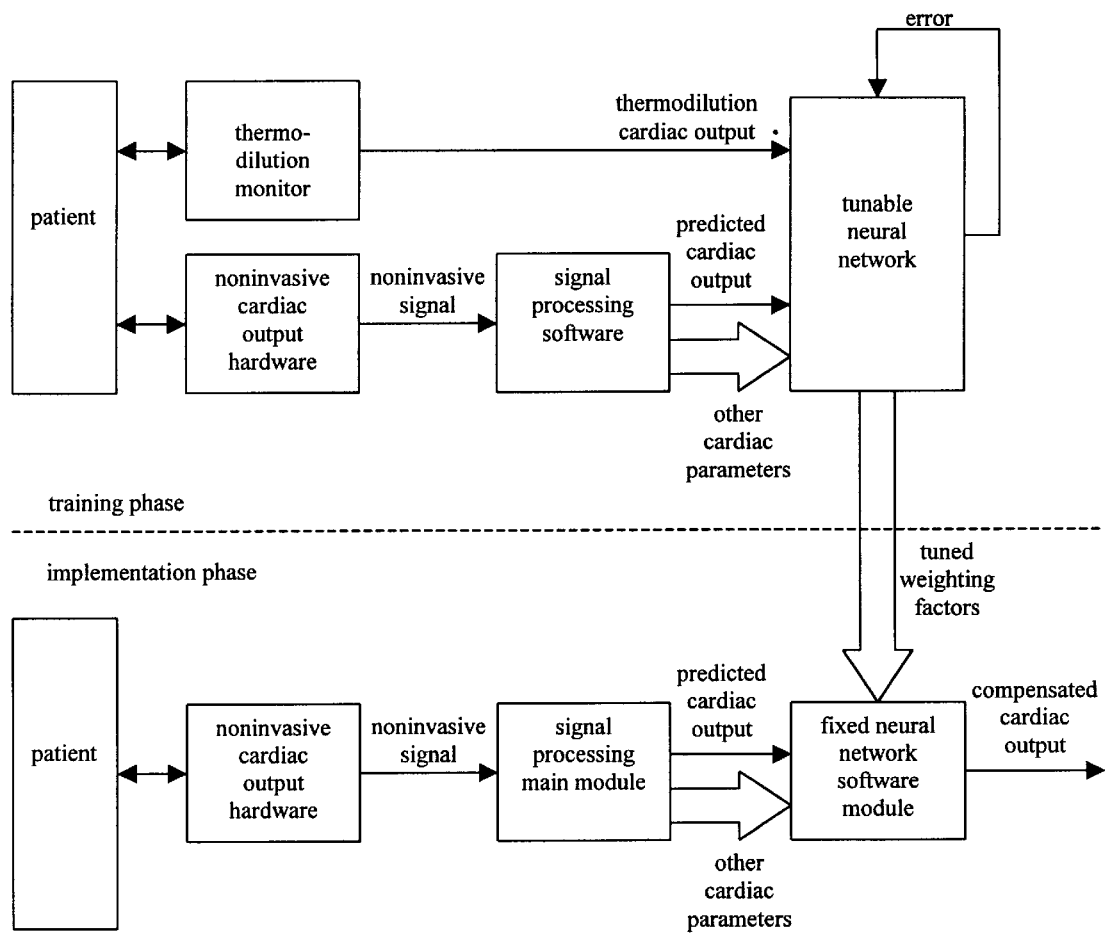
FIG. 3 graphically depicts the training and post-training phases of the embodiment of the invention depicted in FIG. 1.

To determine the converged values of the feedforward neural network weights, clinical patient data is used. Thermodilution and thoracic impedance data will have been concurrently recorded from a group of patients. For each set of data, the network is trained by presenting the predicted CO and appropriate patient parameters as inputs and the thermodilution CO as the desired output. Neural network weights, which have been initialized to small random values, are modified using back propagation of error until a convergence criterion has been reached. Back propagation of error is a methodology well known to those skilled in the art of neural networks. The converged weights and Equation 1 are then programmed as a software module. Consequently, predicted CO and other patient parameters pass through the feedforward neural network possessing the converged weights. The network then tunes the prediction and outputs CCO. This process is illustrated in FIG. 3.

The present invention introduces an application of neural networks for calculation of CO based on direct measurement of other parameters, i.e. cardiac impedance, by non-invasive means. Such estimations are feasible where a physiological event such as CO can be monitored based on generation of a sequence of signals which are quantitatively dependent upon the variable physiological parameter. The only time an invasive monitoring procedure, such as thermodilution, is employed is in the training phase, in order to force a correlation between the invasive and non-invasive monitoring.

The neural network can be trained to compute estimates of CO from non-invasive measurements of impedance cardiography curves by forcing the weights assigned during training to produce an output signal which correlates to a thermodilution curve produced by sampling pulmonary artery blood temperatures using a thermistor at the catheter tip, and measurement of coolant before and after injection into the right ventricle. Because the network processes the entire curve rather than trying to identify particular points such as maximum and minimum, the network is inherently less sensitive to noise than standard signal processing algorithms. The major strength of the neural network lies in its ability to provide nonlinear processing of the input curve, preventing the fluctuations of the curve produced by noise from affecting the overall signal analysis.

An advantage of the neural network is the ease with which it is implemented. Once the neural network weights are calculated from the training phase, they are programmed, along with Equation 1, into a software module of the monitor. Within this embedded systems module, the impedance cardiography parameter values are then modified by the neural network weights using Equation 1. The output of this simple software calculation is the CCO. Should improvement be made to the invasive method to which noninvasive CO output methods are compared, the neural network weights can be recalculated during a new training phase. The weight values would then be updated in a software revision.

Thus, in preparing a compensated estimation of CO (CCO), the neural network is trained and weighting factors determined by a method comprising (a) generating a sequence of non-invasive cardiography signals which are quantitatively dependent upon CO; (b) transmitting and processing the signals within a computer system and associated neural network capable of generating a single output signal for the combined input signals; (c) determining a value for the CO parameter by invasive cardiography concurrent with the generation of signals of steps (a–b), (d) applying weighting factors within the neural network at interconnecting nodes to force the output signal of the neural network to match the known value of the parameter as determined in step (c), (e) recording the input signals and weighting factors as training data within memory of the computer, and (f) repeating steps (a–e) to develop sufficient training data to enable the neural network to accurately estimate parameter value upon future receipt of input signals.

Reporting of Compensated Cardiac Output

The processor typically also formats the binary data signals for real time or essentially real time display on the video monitor. Typically, at least the CCO, dZ/dt and the ECG signals from the preprocessor are displayed for the clinician on the monitor; the $Z_0$ signal and the $\delta Z$ signal are also typically simultaneously displayed for the clinician who can check the validity of the various signals as they are being acquired. At a minimum, the system processes the impedance and ECG signal data to determine at least the HR and the CO of the patient in at least near real time and displays those values. These and other values determined by the present method and apparatus may be printed out on a hard copy printer as well.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

What is claimed is:

1. A method for noninvasive, continuous determination of cardiac output comprising:

(a) generating a sequence of noninvasive cardiography signals which are quantitatively dependent upon cardiac output;

(b) transmitting said sequence of noninvasive cardiography signals to a computer system and associated neural network programmed to be capable of generating a single output signal from the combined sequence of signals;

(c) processing said sequence of signals according to the programming incorporated in said computer system and associated neural network by:

(i) applying previously-determined weighting factors incorporated in said neural network to said sequence of signals, which weighting factors cause the output signal of the neural network to match the value of cardiac output determined, by invasive cardiography signals, to correspond to said sequence of noninvasive cardiography signals; and (d) reporting said single output signal as the determined value of cardiac output corresponding to said sequence of noninvasive cardiography signals.

2. The method for determination of cardiac output as recited in claim 1 wherein said previously-determined weighting factors incorporated in said neural network are determined during a training phase which utilizes concurrent invasive and noninvasive patient cardiac output data.

3. The method for determination of cardiac output as recited in claim 1 wherein said sequence of noninvasive cardiography signals are generated by impedance cardiography.

4. A method for noninvasive, continuous determination of cardiac output as recited in claim 1 wherein the known value of cardiac output is determined by an indicator-dilution technique.

5. A method for noninvasive, continuous determination of cardiac output as recited in claim 4 wherein the known value of cardiac output is determined by thermodilution.

6. A method for noninvasive, continuous determination of cardiac output as recited in claim 1 wherein the sequence of non-invasive cardiography signals are generated by a partial carbon dioxide rebreathing technique.

7. A method for noninvasive, continuous determination of cardiac output as recited in claim 1 wherein the sequence of non-invasive cardiography signals are generated by an echo-doppler technique.

* * * * *